United States Patent [19]

Cottman

[11] Patent Number: 5,053,540
[45] Date of Patent: * Oct. 1, 1991

[54] PREPARATION OF A PARA-AMINODIPHENYLAMINE

[75] Inventor: Kirkwood S. Cottman, Akron, Ohio

[73] Assignee: The Goodyear Tire & Rubber Company, Akron, Ohio

[*] Notice: The portion of the term of this patent subsequent to Nov. 6, 2007 has been disclaimed.

[21] Appl. No.: 490,222

[22] Filed: Mar. 8, 1990

[51] Int. Cl.$^5$ ............................................. C07C 209/24
[52] U.S. Cl. .................................... 564/397; 552/301; 564/396
[58] Field of Search .................. 564/396, 397; 552/301

[56] References Cited

U.S. PATENT DOCUMENTS

| | | | |
|---|---|---|---|
| 1,867,105 | 7/1932 | Schirmacher et al. | 552/301 |
| 3,875,227 | 4/1975 | Kroll et al. | 564/99 |
| 4,045,170 | 8/1977 | Kalopissis et al. | 552/302 |
| 4,355,180 | 10/1982 | Goetz et al. | 564/396 |
| 4,429,157 | 1/1984 | Disteldorf et al. | 564/396 |
| 4,968,843 | 11/1990 | Cottman | 564/397 |

FOREIGN PATENT DOCUMENTS 0453546 12/1948 Canada .............................. 564/397
0774794 5/1957 United Kingdom ................ 552/301

Primary Examiner—Glennon H. Hollrah
Assistant Examiner—Susan P. Treanor
Attorney, Agent, or Firm—Bruce J. Hendricks

[57] ABSTRACT

The present invention relates to a process for the preparation of a p-aminodiphenylamine comprising reacting N-phenylquinoneimine of the formula:

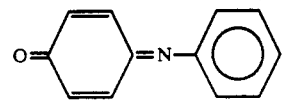

with ammonia, ammonium hydroxide or mixtures thereof, wherein the molar ratio of N-phenylquinoneimine to $NH_3$ in the reaction mixture ranges from about 1:1 to 1:80.

10 Claims, No Drawings

PREPARATION OF A PARA-AMINODIPHENYLAMINE

BACKGROUND OF THE INVENTION

The present invention relates to a unique method for preparing p-aminodiphenylamine from N-phenylquinoneimine. P-aminodiphenylamine is useful in the production of numerous rubber chemicals such as antidegradants, gel inhibitors and polymerization inhibitors.

P-aminodiphenylamine (also known as N-phenyl-p-phenylenediamine) has been made by a variety of methods known to those skilled in the art. For example, Japanese Application 125343-1981 discloses a process for the preparation of N-phenyl-p-phenylenediamine by reacting N-arylaminophenol with ammonia in the presence of an acidic catalyst and polycyclic aromatic compound. The process disclosed in Japanese Application No. 125343-1981 is characterized by a one step, one pot procedure. However, preparation of the products by this procedure would necessitate the use of elaborate distillation equipment to remove the polycyclic aromatic compounds that are employed. The removal of the polycyclic aromatic compounds further contributes to the expense of manufacturing the p-aminodiphenylamine. Since demand for p-aminodiphenyamine is on the increase, there is a need for a new and more efficient process for its production.

SUMMARY OF THE INVENTION

The present invention relates to a process for the preparation of p-aminodiphenylamine by reacting N-phenylquinoneimine with ammonia, ammonium hydroxide or mixtures thereof.

DETAILED DESCRIPTION OF THE PREFERRED EMBODIMENTS

There is disclosed a process for the preparation of a p-aminodiphenylamine comprising reacting N-phenylquinoneimine of the formula:

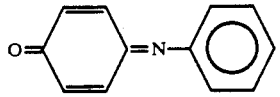

with ammonia, ammonium hydroxide or mixtures thereof wherein the molar ratio of N-phenylquinoneimine to NH3 in the reaction mixture ranges from about 1:1 to 1:80.

There also is disclosed a process for the preparation of p-aminodiphenylamine comprising (a) oxidizing hydroxydiphenylamine to form a N-phenylquinoneimine of the formula:

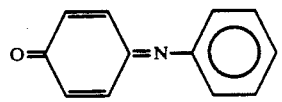

(b) isolating said N-phenylquinoneimine; and (c) reacting said N-phenylquinoneimine with ammonia, ammonium hydroxide or mixtures thereof, wherein the molar ratio of N-phenylquinoneimine to NH3 in the reaction mixture ranges from about 1:1 to 1:80.

The starting materials from the reaction are N-phenylquinoneimine and ammonia, ammonium hydroxide or mixtures thereof. In a preferred embodiment, the N-phenylquinoneimine does not contain more than 5 weight percent hydroxydiphenylamine. In the most preferred embodiment, no or only trace amounts will be present. With an increasing amount of hydroxydiphenylamine, there is an increasing hinderance of completion of the reaction to yield the desired product.

The N-phenylquinoneimine may be prepared by the simple oxidation of hydroxydiphenylamine. For example, the hydroxydiphenylamine may be dissolved in a suitable solvent and oxidized. Examples of solvents which may be used include acetone, methylisobutylketone, tetrahydrofuran and toluene. Preferably a water soluble solvent is used such as the acetone. The hydroxydiphenylamine is oxidized with an oxidizing agent. Representative oxidizing agents include sodium dichromate or potassium dichromate in conjunction with an acid, such as acetic acid. The reaction temperature of the oxidation reaction may vary but is generally from about 20° C. to about 100° C. The preferred reaction temperature ranges from about 25° C. to about 70° C.

Typically the oxidation reaction may be conducted by dissolving the hydroxydiphenylamine in a solvent such as acetone followed by the addition of acetic acid. Aqueous potassium or sodium chromate is then added between 20° and 50° C. The molar ratio of hydroxydiphenylamine to $Cr_2O_7$ is from about 7:1 to 1:3. Preferably a molar ratio of 2:1 to 1:1 is used. Sufficient amount of acid should be present to solubilize its dichromate. Operable amounts of acid based on the moles of hydroxydiphenylamine range from about 2:1 to 1:3 of hydroxydiphenylamine to moles of acid (based on $H+$). The N-phenylquinoneimine product forms instantaneously and can be isolated by adding the oxidation solution to excess cold water. The precipitated product is then filtered, washed with water and dried.

The molar ratio of the N-phenylquinoneimine to ammonia or ammonium hydroxide may vary. Generally speaking, the molar ratio of N-phenylquinoneimine to the ammonia or ammonium hydroxide (based on NH3 content) ranges from about 1:1 to about 1:80, with a ratio of from about 1:1 to about 1:5 being preferred and a ratio of from about 1:1 to 1:3 being particularly preferred.

The reaction of the N-phenylquinoneimine with the ammonia or ammonium hydroxide may be conducted in the presence or in the absence of a solvent. Examples of solvents which may be used in the present invention include methanol, tetrahydrofuran, ethanol, isopropyl alcohol, benzene, toluene, xylene, methylene chloride, ethylbenzene, and the like. Preferably, the solvent is methanol, ethanol or isopropyl alcohol. The reaction between the N-phenylquinoneimine and the ammonia or ammonium hydroxide may be conducted at a variety of temperatures. Generally speaking, the temperature of the reaction ranges from about 15° C. to about 60° C. with a range of about 20° C. to about 40° C. being preferred depending on the boiling point of the reactants and solvent. In a particularly preferred embodiment, the reaction is conducted at room temperature. At reaction temperatures above room temperature, one should conduct the reaction in a closed vessel resulting in a pressure above one atmosphere.

Following the reaction between the N-phenylquinoneimine and the ammonia or ammonium hydroxide, various amounts of N-phenyl-N'-diimine may be present. In an effort to further increase the amount of yield of p-aminodiphenylamine the reaction mixture may be hydrogenated. The reaction mixture is hydrogenated to convert the diimine to p-aminodiphenylamine.

Representative catalysts for the hydrogenation reaction are platinum on carbon, palladium on carbon, Girdler G-22 copper chromite-barium promoted, aqueous sodium hydrosulfite and the like. High temperatures and pressures may be required if the Girdler G-22 catalyst is used. The hydrogenation is preferably done near room temperature with palladium on carbon.

The following examples are included for purposes of illustrating but not limiting the present invention.

EXAMPLE 1

Preparation of N-phenylquinoneimine

Into a suitable reaction vessel, 200 grams of hydroxydiphenylamine was dissolved in 800 ml of acetone at 40° C. 160 grams of acetic acid was added. Into a separate reaction vessel, 320 grams of potassium dichromate ($K_2Cr_2O_7$) was dissolved in 1800 grams of water. The chromate solution was then added to the reaction vessel containing the hydroxydiphenylamine at a temperature ranging from about 38 to 42° C. Within 25 minutes, 100 percent of the hydroxydiphenylamine was oxidized to N-phenylquinoneimine. The reaction product was stirred below 40° C. for an additional 20 minutes and then 300 ml portions of the reaction mixture were added to 1500 ml portions of ice water and filtered. 175 grams of crude product having a purity of 89.9 percent N-Phenylquinoneimine was recovered. Upon subsequent crystallization, following a filtration which removed the salts, the purity was approximately 97.2 weight percent.

EXAMPLE 2

Preparation of p-aminodiphenylamine

Into a 4 ounce reaction bottle was placed 1 gram of 4-phenylquinoneimine (QI) and 25 grams of methanol. To the solution was added 24 grams of ammonium hydroxide (28 percent by weight $NH_3$) The molar ratio of QI to $NH_3$ content was 1:80. The reaction bottle was maintained at room temperature while rotating on a bottle roller for 23 hours. The reaction product was sampled periodically and the samples were tested by gas chromatographic analysis as shown in Table I. By gas chromatographic analysis, the end product contained 27% p-aminodiphenylamine.

TABLE I

| Component | 0 Hr. | 0.5 Hr. | 1 Hr. | 2 Hr. | 3 Hr. | 4 Hr. | 5.5 Hr. | 6 Hr. | 7 Hr. | 23 Hr. |
|---|---|---|---|---|---|---|---|---|---|---|
| QI | 98 | 54.4 | 30.0 | 37.0 | 28.0 | 28.0 | 24.0 | 28.0 | 35.0 | 28.0 |
| Unknown | — | — | — | — | — | — | — | — | — | 1.6 |
| HDPA[1] | — | 10.1 | 26.0 | 21.0 | 27.0 | 27.0 | 30.0 | 26.0 | 18.0 | 13.5 |
| p-aminodiphenylamine | — | 15.0 | 17.0 | 18.0 | 18.0 | 18.0 | 19.0 | 20.0 | 19.0 | 27.0 |
| Unknown | — | 19.0 | 21.0 | 22.0 | 22.0 | 21.0 | 22.0 | 23.0 | 23.0 | 28.0 |
| Unknown | — | — | 1.5 | — | 1.3 | 1.4 | 1.3 | 1.0 | — | — |
| Unknown | — | — | 3.9 | 2.4 | 3.7 | 2.3 | 3.0 | 2.0 | 4.6 | — |

[1]Hydroxydiphenylamine
All of the gas chromatographic samples were dissolved in THF before analyzing.

EXAMPLE 3

Preparation of p-aminodiphenylamine

Into a 4 ounce reaction bottle was added 1 gram of N-phenylquinoneimine (QI), 6.2 grams of ammonium hydroxide (28% by weight $NH_3$) and 25 grams of methanol. The molar ratio of QI to $NH_3$ content was 1:20. The reaction bottle was capped and maintained at room temperature while rotating on a bottle roller for 21 hours. The reaction mixture was sampled periodically and the samples were tested by gas chromatographic analysis as shown in Table II. After the 21 hour period, the reaction bottle was charged with 8 grams of additional ammonium hydroxide (28% by weight $NH_3$). By gas chromatographic analysis, the reaction product contained 42.0% p-aminodiphenylamine.

TABLE II

| Component | 0 Hr. | 1 Hr. | 2 Hr. | 3 Hr. | 4 Hr. | 21 Hr. | 26 Hr. |
|---|---|---|---|---|---|---|---|
| QI | 98.0 | 67.0 | 52.0 | 43.0 | 39.0 | 33.0 | 16.0 |
| Unknown | — | 5.3 | 1.6 | 1.4 | — | — | — |
| HDPA[1] | — | — | — | — | — | 1.0 | 14.0 |
| p-aminodiphenylamine | — | 11.5 | 23.2 | 29.0 | 35.0 | 39.0 | 42.0 |
| Unknown | — | 13.4 | 19.0 | 23.2 | 24.0 | 24.8 | 22.5 |
| Unknown | — | — | — | — | — | — | 1.3 |
| Unknown | — | — | 1.6 | — | — | — | — |
| Unknown | — | — | 2.3 | 2.5 | 2.6 | 3.0 | 3.0 |

[1]Hydroxydiphenylamine
All of the gas chromatographic samples were dissolved in the THF before analyzing.

EXAMPLE 4

Preparation of p-aminodiphenylamine

Into a 4 ounce reaction bottle was weighed 1 gram of N-phenylquinoneimine (QI), 25 grams methanol and 3.1 grams of ammonium hydroxide (28% by weight $NH_3$). The molar ratio of QI to $NH_3$ content was 1:10. The bottle was capped and allowed to rotate at room temperature on a bottle roller for 20.5 hours. During the 20.5 hours the reaction mixture was sampled and tested by gas chromatographic analysis. As shown in Table III, gas chromatographic analysis after 20.5 hours of reaction showed that the reaction product contained 45% of p-aminodiphenylamine.

TABLE III

| Component | 0 Hr. | 1 Hr. | 2 Hr. | 3 Hr. | 4 Hr. | 4.5 Hr. | 5 Hr. | 9 Hr. | 20.5 Hr. | 20.5 Hr.[2] |
|---|---|---|---|---|---|---|---|---|---|---|
| QI | 98 | 87.0 | 73.0 | 63.0 | 50.0 | 44.0 | 44.0 | 28.0 | 20.0 | — |
| Unknown | — | 1.0 | 1.1 | — | — | — | — | — | — | — |
| HDPA[1] | — | — | — | — | 1.4 | 3.0 | 3.6 | 3.7 | 7.1 | 30.0 |
| p-aminodiphenylamine | — | 6.4 | 15.5 | 23.3 | 31.0 | 33.1 | 36.0 | 43.0 | 45.0 | 46.0 |
| Unknown | — | 4.8 | 10.1 | 14.0 | 17.2 | 18.5 | 19.1 | 23.0 | 25 | — |
| Unknown | — | — | — | — | — | — | — | — | 1.0 | 23.0 |

TABLE III-continued

| Component | 0 Hr. | 1 Hr. | 2 Hr. | 3 Hr. | 4 Hr. | 4.5 Hr. | 5 Hr. | 9 Hr. | 20.5 Hr. | 20.5 Hr.[2] |
|---|---|---|---|---|---|---|---|---|---|---|
| Unknown | — | 1.3 | 0.7 | — | — | — | — | — | 0.5 | 0.8 |
| Unknown | — | — | — | — | — | 1.8 | 1.0 | 1.7 | 1.8 | — |

[1]Hydroxydiphenylamine
[2]Sample reduced with aqueous sodium hydrosulfite at room temperature
All gas chromatographic samples were dissolved in THF before analyzing

EXAMPLE 5

Preparation of p-aminodiphenylamine

Into a 4 ounce reaction bottle was weighed 1 gram of N-phenylquinoneimine (QI), 25 grams of methanol and 1.5 grams of ammonium hydroxide (28% by weight NH$_3$). The molar ratio of QI to NH$_3$ content was 1:5. The bottle was capped and allowed to rotate at room temperature on a bottle roller for 96 hours. During the 96 hours, the reaction mixture was sampled and tested by gas chromatographic analysis. As shown in Table IV, gas chromatographic analysis after 96 hours of reaction showed that the reaction product contained 48% of p-aminodiphenylamine.

TABLE IV

| Component | 0 Hr. | 1 Hr. | 2 Hr. | 3 Hr. | 4 Hr. | 5 Hr. | 6 Hr. | 6.7 Hr. | 23 Hr. | 96 Hr. |
|---|---|---|---|---|---|---|---|---|---|---|
| QI | 98.0 | 91.0 | 86.0 | 76.0 | 71.0 | 67.0 | 59.0 | 56.0 | 30.0 | 25.0 |
| Unknown | — | 1.3 | 0.8 | 0.9 | 0.8 | 0.8 | 0.3 | 0.1 | — | — |
| HDPA[1] | — | — | — | — | — | — | — | — | 4.0 | 5.5 |
| p-aminodiphenylamine | — | 5.5 | 8.6 | 13.6 | 17.5 | 22.2 | 28.4 | 30.0 | 45.3 | 48.0 |
| Unknown | — | 2.6 | 4.7 | 7.1 | 8.9 | 9.8 | 12.8 | 14.0 | 21.2 | 21.0 |

[1]Hydroxydiphenylamine
All gas chromatographic samples were dissolved in THF before analyzing

EXAMPLE 6

The procedure and amount of reactants of Example 5 was repeated except that NH$_3$ gas was used in place of NH$_4$OH. The mole ratio of QI to NH$_3$ gas was 1:5. Table V below lists the data from the gas chromatographic analysis.

TABLE V

| Component | 0 Hr. | 1 Hr. | 3.3 Hr. | 4 Hr. | 6.3 Hr. | 24 Hr. | 30 Hr. | 72 Hr. | 96 Hr. |
|---|---|---|---|---|---|---|---|---|---|
| QI | 98.0 | 91.0 | 74.0 | 67.2 | 54.0 | 21.0 | 26.5 | 24.0 | 25.0 |
| Unknown | — | — | — | 1.4 | — | — | — | — | — |
| HDPA[1] | — | — | — | — | — | 5.7 | — | 0.1 | 5.5 |
| p-aminodiphenylamine | — | 4.3 | 13.6 | 19.9 | 29.1 | 49.2 | 49.0 | 51.0 | 48.0 |
| Unknown | — | 2.8 | 9.1 | 11.2 | 19.1 | 22.0 | 25.0 | 25.0 | 21.0 |

[1]Hydroxydiphenylamine
All gas chromatographic samples were dissolved in THF before analyzing

EXAMPLE 7

Into a 4 ounce reaction bottle was weighed 10 grams of methanol and 0.55 grams of NH$_3$ gas. To the bottle was next added 15 grams of toluene which contained 1.0 gram of QI. The reaction bottle was rotated at room temperature for 144 hours and sampled as shown in Table VI.

TABLE VI

| Component | 0 Hr. | 3 Hr. | 4 Hr. | 21 Hr. | 48 Hr. | 72 Hr. | 72 Hr.[2] | 72 Hr.[3] | 144 Hr. | 144 Hr.[3] |
|---|---|---|---|---|---|---|---|---|---|---|
| QI | 99.0 | 92.5 | 90.0 | 49.3 | 20.0 | 17.6 | — | 3.5 | 11.3 | 5.4 |
| Unknown | — | 2.5 | 3.1 | 8.1 | 1.5 | 1.2 | — | — | 6.6 | — |
| HDPA[1] | — | — | — | — | — | — | 10.1 | 7.5 | — | 2.5 |
| p-aminodiphenylamine | — | 1.7 | 2.4 | 26.2 | 50.0 | 51.0 | 66.7 | 71.8 | 55.5 | 70.2 |
| Unknown | — | 1.7 | 2.9 | 16.2 | 27.0 | 30.0 | 0.6 | 13.0 | 31.0 | 21.0 |
| Unknown | — | — | — | — | — | — | 21.6 | 1.6 | — | — |
| Unknown | — | — | — | — | — | — | — | 1.2 | 1.2 | 0.6 |
| Unknown | — | — | — | — | — | — | 0.5 | 0.5 | 0.6 | 0.5 |

[1]Hydroxydiphenylamine
[2]Sample reduced with aqueous sodium hydrosulfite at room temperature
[3]Sample was analyzed neat without any THF solvent
All gas chromatographic samples were dissolved in THF before analyzing except as indicated above

What is claimed is:
1. A process for the preparation of p-aminodiphenylamine comprising reacting N-phenylquinoneimine of the formula:

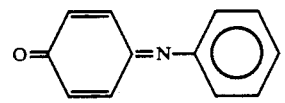

with ammonia, ammonium hydroxide or mixtures thereof wherein the molar ratio of N-phenylquinoneimine to NH$_3$ in the reaction mixture ranges from about 1:1 to 1:80 and the reaction is conducted at a temperature ranging from about 15° C. to about 60° C.

2. A process of claim 1 wherein ammonium hydroxide is used.

3. A process of claim 1 wherein ammonia is used.

4. A process of claim 1 wherein the reaction is conducted in the presence of a solvent selected from the group consisting of methanol, tetrahydrofuran, ethanol, isopropyl alcohol, benzene, toluene, xylene, methylene chloride, ethylbenzene and cumene.

5. The process of claim 4 wherein said solvent is methanol.

6. The process of claim 1 wherein said reaction is conducted at a temperature ranging from about 20° C. to 40° C.

7. The process of claim 6 wherein said reaction is conducted at room temperature.

8. A process for the preparation of a p-aminodiphenylamine comprising (a) oxidizing hydroxydiphenylamine to form N-phenylquinoneimine of the formula:

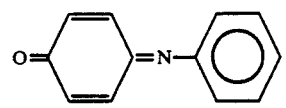

(b) isolating said N-phenylquinoneimine: and (c) reacting said N-phenylquinoneimine with ammonia, ammonium hydroxide or mixtures thereof, wherein the molar ratio of N-phenylquinoneimine to $NH_3$ ranges from about 1:1 to 1:80.

9. A process of claim 8 wherein ammonium hydroxide is used.

10. A process of claim 8 wherein ammonia is used.

* * * * *